United States Patent [19]
Stoner et al.

[11] 3,961,191
[45] June 1, 1976

[54] CODED IMAGING SYSTEMS

[75] Inventors: William W. Stoner, Watertown; David T. Wilson, Billerica; Harrison H. Barrett, Lexington, all of Mass.

[73] Assignee: Raytheon Company, Lexington, Mass.

[22] Filed: June 26, 1974

[21] Appl. No.: 483,273

[52] U.S. Cl. .............................. 250/312; 250/321; 250/368
[51] Int. Cl.² ........................................... G03C 9/00
[58] Field of Search .......... 250/366, 367, 336, 361; 350/160 ZP

[56] References Cited
UNITED STATES PATENTS

| | | |
|---|---|---|
| 2,730,566 | 1/1956 | Bartow et al. ...................... 250/369 |
| 3,748,470 | 7/1973 | Barrett ............................... 250/366 |
| 3,792,273 | 2/1974 | Bergstedt ........................... 250/369 |
| 3,840,747 | 10/1974 | Macovski ........................... 250/369 |

*Primary Examiner*—Harold A. Dixon
*Attorney, Agent, or Firm*—David M. Warren; Joseph D. Pannone; Milton D. Bartlett

[57] ABSTRACT

A nuclear imaging system in which a substantially on-axis Fresnel zone plate positioned between a source of nuclear radiation in living tissue and a spatial detector is moved in a predetermined time sequence in synchronism with motion of a bar pattern formed at the spatial detector output to improve suppression of unwanted spatial frequency components and to facilitate production of an image of the nuclear source.

15 Claims, 11 Drawing Figures

CODED IMAGING SYSTEMS

BACKGROUND OF THE INVENTION

Application Ser. No. 250,224 filed May 4, 1972, now U.S. Pat. No. 3,829,688 by Harrison H. Barrett discloses a nuclear shadowgraph system for forming large area nuclear images with zero order data components suppressed by using an off-center section of a Fresnel zone plate and with the low frequency components enhanced by the addition of a carrier frequency through a second nuclear mask. Such a system substantially increases the spatially detected count rate over conventional collimated or pinhole scanned imaging systems. However, as pointed out in said application, for higher energy radiation the relatively thick scintillometer crystals limit the definition, or upper frequency response, of the spatial detector system, and commercially available spatial detector amplifier systems, such as the Anger camera, having upper spatial frequency limits below the spatial frequency desired for a carrier frequency can be used.

SUMMARY OF THE INVENTION

This invention provides for a nuclear detecting system where the zero spatial frequency component may be partially or substantially completely suppressed by means comprising means for shifting the phase of the spatial code of the nuclear radiation pattern.

This invention further discloses that with such suppression substantially on-axis Fresnel coding patterns of nuclear radiation or cancellation can be used having relatively low spatial frequencies so that the spatial detection and/or system need have only a relatively low spatial frequency response.

More specifically, this invention discloses spatial conversion of a radiation having a first code pattern having an upper energy intensity level above the visible range, such as nuclear radiation, to a spatial radiation pattern of a lower, and preferably visible, energy level and then combining said first spatial code pattern in said lower energy radiation with a second spatial code pattern having at least one spatial frequency which is higher than, and preferably greater than, twice the highest spatial frequency of said first spatial code pattern. Thus, the spatial detector and/or spatial amplifier for detecting and/or amplifying the upper intensity level radiation requires a spatial frequency response only high enough to pass the highest spatial frequency of the nuclear radiation.

This invention further discloses a structure for recording the combined pattern for a first predetermined time, then synchronously shifting the spatial phase of both the upper intensity level radiation code pattern and the lower intensity level radiation coding pattern combined therewith by substantially the same phase angle, and recording the combined coded pattern for a second predetermined time substantially equal to the first predetermined time and preferably on the same recording medium. An image can then be constructed from the recorded data in which substantial cancellation of the zero order Fourier plane data is suppressed to improve the image definition and reduce background interference.

BRIEF DESCRIPTION OF THE DRAWINGS

Other and further embodiments of this invention will be apparent as the description thereof progresses, reference being had to the accompanying drawings wherein.

DESCRIPTION OF THE PREFERRED EMBODIMENT

Figure 1:
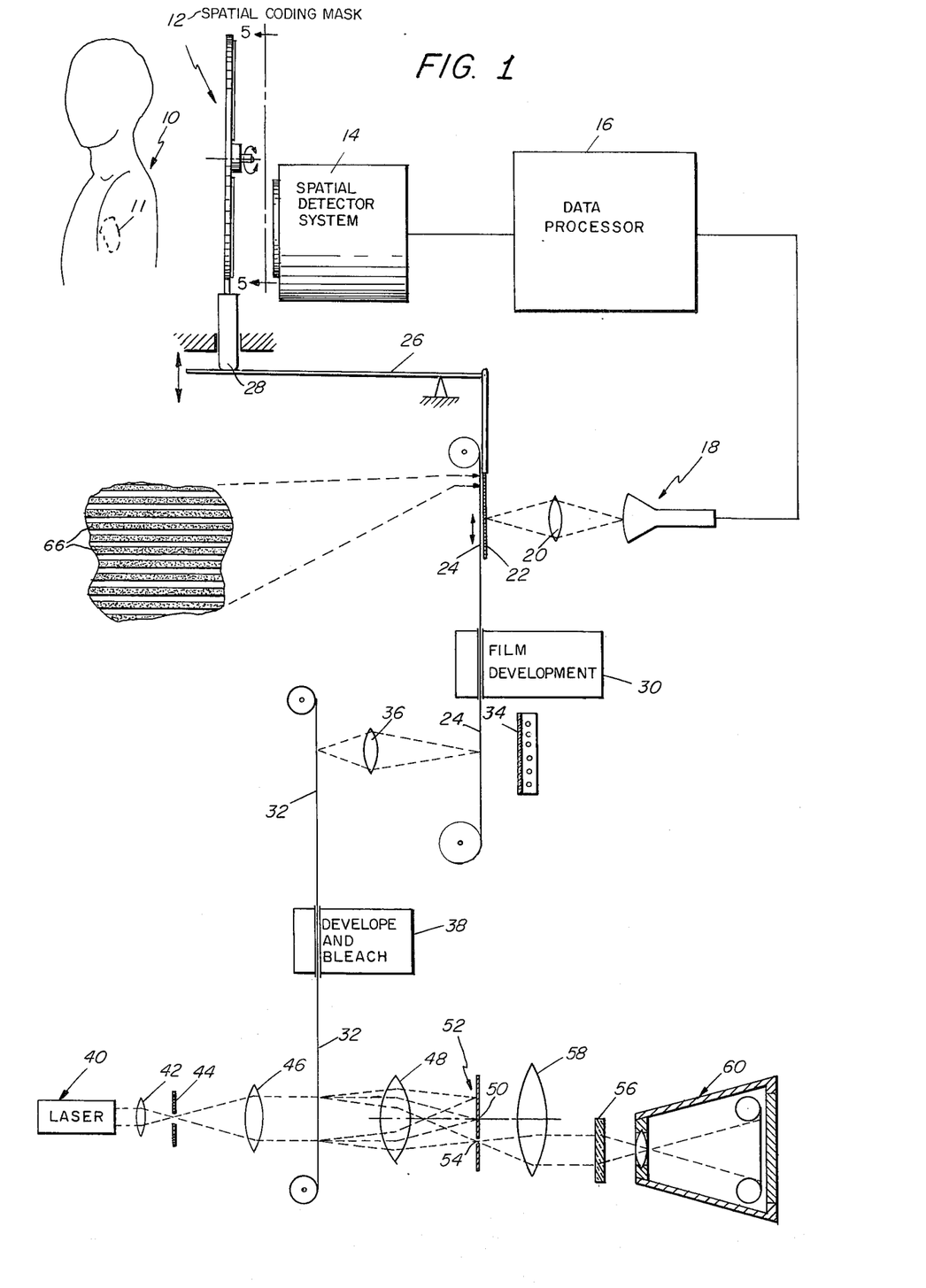
FIG. 1 illustrates a diagram of a system embodying the invention wherein two opposite phase nuclear radiation spatially coded masks are shifted synchronously with a visible radiation spatially coded mask to form a composite shadowgraph.

Referring now to FIG. 1, there is shown a system for detecting the positional source of nuclear radiation emanating from an object 10, such as the heart or lung area of a person who has injested a radiopharmaceutical. Spatial coding of the nuclear radiation is achieved by a mask structure 12, and spatial detection of such spatially coded emanations is achieved by a spatial detector system 14 which also amplifies the spatially detected pattern and feeds the pattern to a data processor 16 which supplies deflection and brightness control signals to a cathode ray tube 18 for displaying the detected signals as bright spots, projecting such spots via a lens 20 through a mask 22 to a film 24.

The mask 22 is moved in synchronism with the support carrying the multiple mask structure 12 by means of a lever 26 and cam follower 28.

The film 24, after being exposed through mask 22, is developed by a developer 30.

Light from a box 34 containing a plurality of lights illuminates the film 24 through a ground glass screen to provide diffused light so that points on film 24 transmit light proportional to their exposure. The light pattern is then focused by means of a lens system 36 on a second film 32. The positioning of the lens system 36 is preferably chosen to produce a reduction in the pattern size on film 32. The film 24 is preferably chosen to be relatively fast to minimize the exposure time during which the object 10 must remain immobile, while the film 32 is, preferably, relatively slow and thick so that subsequent to exposure it can be developed and bleached with develop and bleach apparatus 38 to render the film 32 substantially transparent with the thickness of the film containing variations in dielectric constant due to the bleach process. As a result, light directed through the film will be selectively focused and refracted by reason of the dielectric lens action of elemental areas of the bleached film 32.

Film 32 may be used to reconstruct an image of the object 10 by directing a beam of substantially coherent light from a laser 40 through a lens 42 and a pinhole iris 44 to produce light emanating substantially entirely from a point source. The beam then passes through lenses 46 and 48 to produce a beam which focuses at a point 50 in a focal plane containing an opaque wall 52 having an opening 54 offset from the axis containing focal point 50. The bleached film 32 positioned between lenses 46 and 48 deflects the light elements as a function of the informational content stored in the film 32 so that individual film elements produce individual Fourier transforms of light elements passing therethrough resulting in deflection of the desired beam elements so that they pass through iris 54. After passing through iris 54, the light pattern is projected as a reconstructed image of object 10 on a viewing surface such as a ground glass screen 56 either directly or, if desired, by means of a lens 58 to reduce the size of the image. The image projected on screen 56 is photographed by a conventional camera 58 or, if desired, the image may be viewed directly.

Tomographic effects may be accomplished by movement of the relative position of the ground glass screen 56 with respect to the film 32. For example, if screen 56 is moved away from the film 32, a different slice of the object 10 will appear in sharp contrast on screen 56, with the remainder of the information appearing as a somewhat fuzzy or frosted background.

The Fresnel zone pattern is formed by making the area of each of the transparent rings equal to the area of each of the opaque spaces. When the structure 12 is rotated, the mask section 64 positioned in front of the detector 14 is replaced by the mask section 62 and simultaneously the mask 22 is moved vertically by the cam 28 and lever 26 for a distance equal to the width of one of the horizontal opaque bars 66 of mask 22 so that the portions of the film which were blocked by the bars 66 are now exposed and those which were previously exposed are now blocked since the width of the bars 66 is preferably substantially equal to the transparent spaces between the bars 66. Since mask section 62 is the supplement to the mask section 64, that is, in terms of phase mask section 64 is $\pi$ radians different, or 180° out of phase with the spatial frequence of the reference code produced by the mask section 62 and shifting of the mask 22 by one bar width is also a shift of $\pi$ radians, the relative phase of both masks 12 and 22 has been maintained constant.

Figure 5:
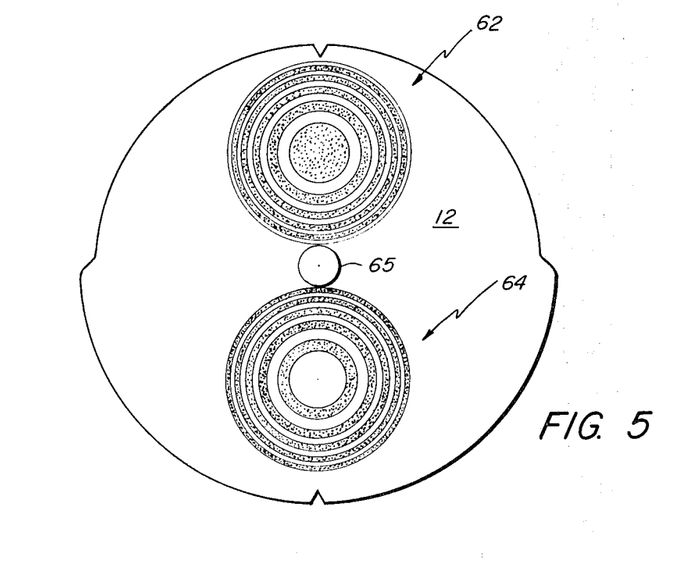
FIG. 5 illustrates a two-phase coding structure for use in the systems of FIG. 1 or FIG. 3.

To substantially completely subtract the undesired background information from the completed picture, mask 24 may be formed, as shown in FIG. 5, of a positive Fresnel zone pattern section 62 and negative Fresnel zone pattern 64. As used herein, the terms positive and negative Fresnel patterns mean the center areas of the two plates are respectively opaque and transparent to nuclear radiation. As shown, the negative section 64 is positioned between the object 10 and detector 14 and film 24 is exposed the total exposure time of the film 24 while the mask 22 is positioned in the position shown. The zone plate sections 62 and 64 are formed, for example, of rings of lead on aluminum so nuclear particles will go through the aluminum but will be stopped by the rings of lead, the result being a shadowgraph of nuclear radiation coded with the Fresnel pattern projected on spatial detector 14. As shown, the center region of mask section 64 is transparent to nuclear particles, and the first ring of lead surrounds the hollow center. As shown, approximately five rings of lead and five intervening spaces are used for the mask sections having an overall diameter of one foot or so. If the mask 22 has 200 horizontal bars spaced over four inches, one bar width is 0.01 inch and, hence, lever 26 pivoting on a fulchrum moves mask 22 vertically 0.01 inch when the mask 12 is rotated 180°.

Any other desired mechanism of synchronizing the motion in time and distance between the mask 22 and the mask 12 could be used. Indeed, if desired, the mask 22 could consist of two plates which could be manually substituted for each other in a fixed structure in the camera head and the bar pattern appropriately moved for each substitution. Furthermore, while the configuration of the mask 22 is shown as a plurality of parallel spaced bars in which the width of the bars equals the spacing between the bars, any desired coding pattern could be used.

The system described thus far has the advantage that the zero order information is cancelled by the interlacing data of the positive and negative zone plates 62 and 64 as alternate bars of data on the film 24, such interlacing being accomplished by the synchronous shifting of the bars of the mask 22. As a result, the iris 54 in stop 52 can be made relatively large since the stop 53 need stop out only the orders of the image other than the zero order which lies along the axis of the reconstruction system and, hence, is closest to the iris 54. The bars in mask 22 are perpendicular to the direction of the offset of the iris 54 in the stop 52 since the bars act as a diffraction grating which diffracts the information in a direction perpendicular to the bars.

Because the zero order information is eliminated by the cancellation process of this system, on-center Fresnel zone patterns, which have large zero order or D.C. background noise, can be used since this data is cancelled, and such patterns having low spatial frequencies near the centers of the patterns transmit large object data and require a smaller number of rings in the zone plate, hence having a lower frequency response. As a result, the detector 14 can be of a relatively low frequency response type, such as an Anger camera which detects scintillations from a relatively thick scintillation crystal positioned in front of the photocells of the detector and thus amplifying signals derived from high energy particles whereas if a large number of rings were required in the zone plates, only limited frequency response could be achieved with the amplifier, and for high definition it has usually been preferable to expose the film directly from the scintillation crystal.

Figure 2:
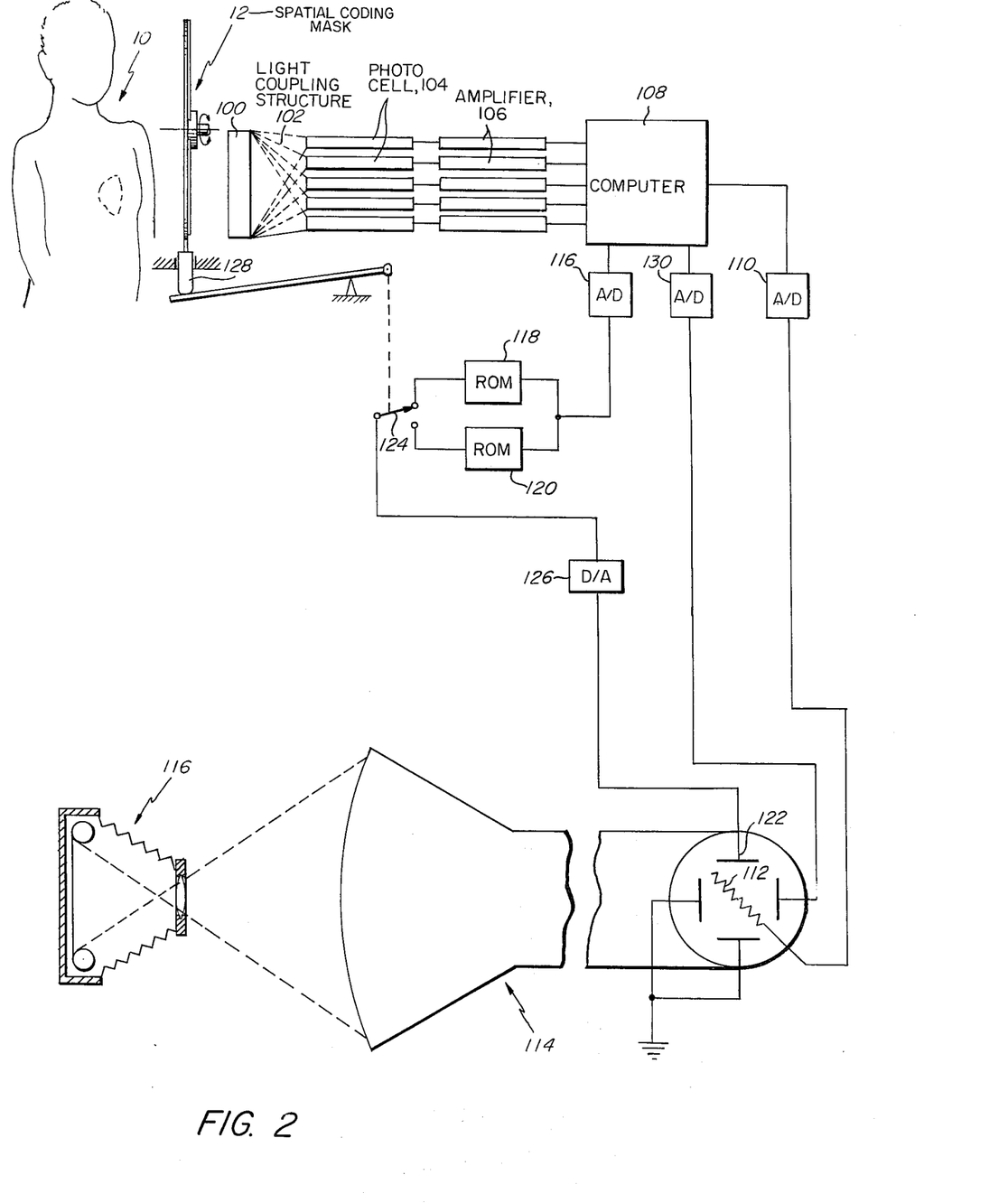
FIG. 2 illustrates an alternate embodiment of a detector amplifier display structure for use in the system of FIG. 1.

Referring now to FIG. 2, there is shown the details of an electronic optical mask altering component for use in the system of FIG. 1. The object 10, having ingested a radiopharmaceutical, emits high energy particles which are coded through a rotary mask structure 12 comprising two zone plates similar to those described in connection with FIG. 1. The radiation emanating through the mask structure is spatially detected by a spatial detecting structure 14. As illustrated herein, structure 14 may have a conventional detecting head comprising a scintillation crystal 100 which produces flashes or scintillations of light upon being struck by nuclear particles. The light from scintillation crystall 100 is conducted by means of a light pipe structure 102 to a plurality of photocells 104 whose outputs are individually amplified in amplifiers 106 and fed to a computer 108 whose output consists of three pulses. A first pulse which is the intensity of the flash of the scintillation is fed through pulse delay 110 to the grid 112 of a cathode ray tube 114. A second of the outputs of the computer 108 comprises the computed Y position of the flash in the scintillation crystal 100 and if fed to an analog-to-digital converter 116 whose output addresses are parallel to read-only memories 118 and 120. The outputs of the read-only memories 116 and 118 supply positional address information for the Y deflection plates 122 of cathode ray tube 114 through a switch 124 and a digital-to-analog converter 126.

Switch 124 is actuated by the rotary position of the mask structure 12 so that it is in the first position to accept information from read-only memory 118 when the positive Fresnel zone plate mask is positioned between the object and the detector and to accept information from read-only memory 120 when the negative mask is positioned in front of the detector. As illustrated herein, switch 124 is manually actuated by a positional cam 128 on structure 112 which performs the desired switching function.

The third output from the computer 108 is a pulse indicative of the X position of the scintillation in the crystal 100 and is fed through a delay 130 to the X deflection plates 132 of cathode ray tube 114. In operation, the read-only memories have two hundred address positions corresponding to two hundred different heights of the Y position pulse from the computer 108 to the analog-to-digital converter 116 requiring, for example, an eight-bit binary address code. Each of the addresses corresponds to one of the bar and adjoining space positions illustrated in FIG. 1. When the switch 124 is in the position shown, the read-only memory 120 is connected through digital-to-analog converter 126 to the deflection plates 122. Addresses correspond to the upper half of each of the bar space positions so that if the cathode ray tube spot size is less than a bar space, for example less than twenty-five percent of the total height of the cathode ray tube face, information supplied to grid 112 is presented on any of two hundred horizontal bars on the face of the cathode ray tube 114. When the switch 124 is shifted to the opposite position, the addresses correspond to the interleaving bar positions equivalent to mechanically moving a mask one bar space vertically as is done in the system of FIG. 1. However, since none of the data is blocked by a mask position but appears on the face of the cathode ray tube, twice the count rate is available.

In accordance with communication theory, the bar spacing preferably produces a spatial bar pattern having a sampling rate at least twice the highest spatial frequency component of the Fresnel zone pattern to be processed and, hece, the actual position of the data in either the upper or lower bar position does not appear in the final data but is rather filtered out by the optical reconstruction system illustrated in FIG. 1.

The output of the cathode ray tube 114 is photographed by a camera 116 whose film is processed, for example, in accordance with the system described in connection with FIG. 1.

The pulse shape and the time of the delays 110 and 130 are designed so that the positional pulses supplied to the deflection plates of the cathode ray tube 114 have been applied for a sufficient length of time for transients to settle down, for example, a few microseconds, before the pulse arrives at the grid 112 to brighten the screen, and the delays 130 and 110 are selected to, in addition, compensate for the time delay of a microsecond or more required for the operation of the read-only memories 118 and 120. It should be clearly understood that both the X and Y coordinates and the cathode ray tube brightening signal from the computer 108 could be digitized and processed in any desired fashion.

DESCRIPTION OF THE PREFERRED METHOD OF OPERATION

Referring now to FIGS. 7 and 8A-D, the preferred method of operation of the system of FIG. 1 and/or FIG. 2 will be disclosed.

A radiopharmaceutical which emits radiation preferably in the intensity range between 100 and 400 electron kilovolts is introduced by any desired means into the object 10 and is predominantly concentrated in an organ thereof, such as the thyroid, lungs, blood vessels or bone structure, and such radiations pass through the positive Fresnel zone plate for a predetermined period of time, such as 10 minutes, and are detected by the detector 14.

The outline of the Fresnel zone plate is illustrated in FIG. 5 and is preferably an on-axis Fresnel zone plate so that the same spatial definition can be achieved with a lower number of total rings than with an off-axis zone plate. As a result, the radiation transparent spacing between the narrowest rings may be wider and, hence, the thickness of the zone plate may be greater for use with higher intensity radiations without blocking images of the radioactive material from the object emitted at angles substantially through the zone plate. Alternatively, for a lower intensity radiation such as that from technetium of one hundred forty electron kilovolts, a thinner zone plate and a larger number of rings may be used thereby permitting a greater definition of the image.

Figure 7:
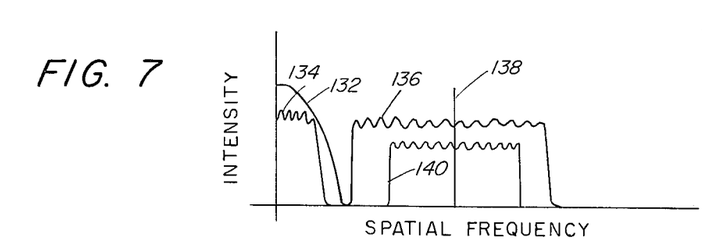
FIG. 7 is a diagram illustrating spatial frequency characteristics of the systems of FIGS. 1 through 4.

In FIG. 7, an example of the spatial frequency response of the camera tube using photocells of FIG. 2 is illustrated by the curve 132 which shows an upper spatial frequency response of, for example, slightly less than one line pair per centimeter. The spatial frequency of one of the on-axis zone plates of FIG. 5 appears as indicated generally by curve 134. In the event that an off-axis zone plate with a half-tone screen were used as set forth in the aforementioned copending application Ser. No. 250,224, the upper frequency response would be much larger, as indicated by the curve 136 surrounding the carrier frequency 138. However, by the use of an on-axis zone plate, lower spatial frequencies can be used to obtain the same information while preserving effectively the lower spatial frequencies containing the information necessary for large body imaging. By the substitution of the bar structure after amplification, the carrier frequency 138 is injected into the data prior to recording by the film which produces an integration of the data.

With the positive Fresnel zone plate 62 and the horizontal bar screen 22 in a first position, a horizontal bar pattern is recorded on the film as a first set of bars having data consisting of carrier frequency 138, with the amplified data in the base band curve 134 modulated thereon as indicated by the curve 140.

The spatial frequency 138 is selected by the number of bars in the screen 22 and preferably is chosen to be at least twice the highest spatial frequency in the curve 134 so that when the data of curve 134 is modulated by carrier 138 to produce the carrier side bands represented by the curve 140, there will be no overlap of the curves 140 and 134 and, hence, no data ambiguity in the recorded shadowgraph.

The zone plate structure 12 is then rotated 180° about hub 65 to place the negative Fresnel zone section 64 before the detector 14, and the screen 22 is moved vertically the width of one bar 21 to shift the phase of the carrier frequency by 180° and the data is recorded in a second set of bars on the film interleaved between the first set of bars for substantially the same length of time as with the positive zone pattern 62.

Figure 8A:
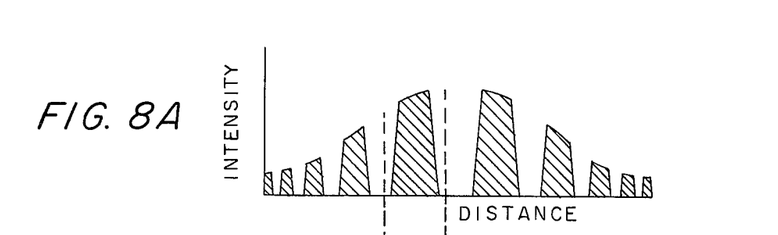
FIGS. 8A through 8D illustrate coding patterns for a point source for the structure of FIG. 4 in the system of FIG. 1.
Figure 8B:
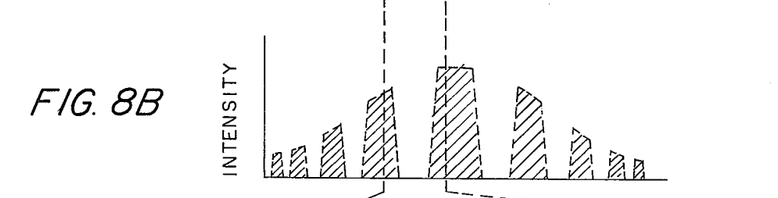
Figure 8C:
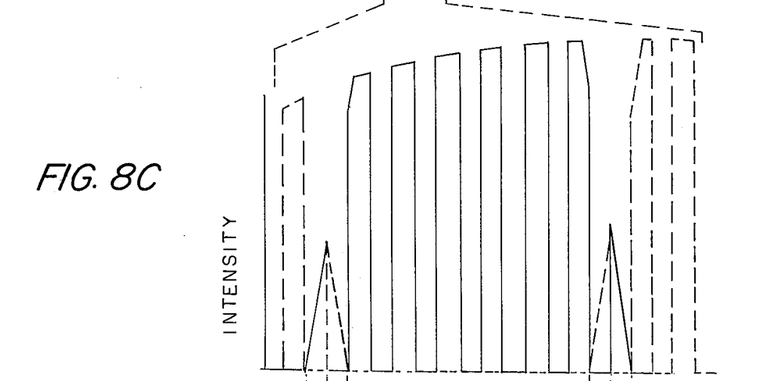
Figure 8D:
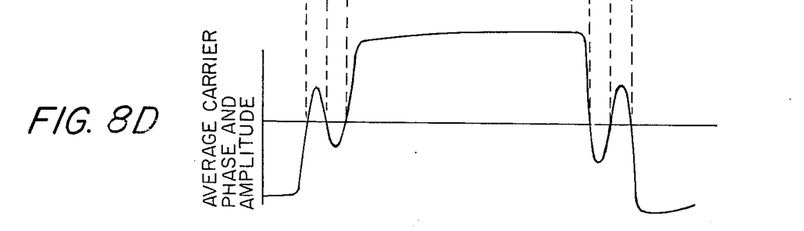

In FIG. 8A there is shown the energy intensity distribution across the face of the detector 14 produced, by way of example, from a single point in the object 10 positioned approximately along the axis of the zone plate and emitting energy through all the spaces between the lead rings of the positive zone plate. FIG. 8B illustrates the same point source radiating through the negative zone plate 64. FIG. 8C shows the intensities recorded through a portion of the bar screen 22 onto the film for both the zone plates indicating the positive zone pattern with solid lines and the negative zone pattern with dotted lines. Where the slightly sloped sides of the two zone plate intensities coincide or slightly overlap, appropriate subtraction and/or phase reversal of the output signal is obtained. The phase and intensity of the data of FIG. 8C are shown in FIG. 4D. FIGS. 8C and 8D have been expanded to show only a portion of the overlap regions of FIGS. 8A and 8B, indicated by the dotted lines between the graphs, and are indicative of the general subtraction process involved. Thus, it may be seen that the data of on-axis zone plates is appropriately preserved and tagged with a reference tag on the film.

The foregoing are by way of example only, and the shape and spacing of the patterns could be of any desired spatial frequency and contour.

Each point source in the object produces a similar set of patterns and subtractions, with the location of the point source with respect to the axis of the zone plate being recorded with amplitude and phase characteristics of the resultant signal. Such signals are in the form of information in the film which upon bleaching of the film in the bleaching step is converted to appropriate amplitude and phase information which has been found to deflect the light from the laser directed therethrough for image construction. The zero order or D.C. background data, however, is cancelled by being oppositely coded by the positive and negative Fresnel zone patterns in adjacent bars of the film.

If desired, the output from the detector, instead of being supplied to the cathode ray tube, can be supplied as digital information to a digital computer using digital storage and Fourier transformation to reconstruct an image which may be displayed on a cathode ray tube or formed in any other type of output recording medium.

Preferably, the time of exposure of the film through each of the zone plates is made the same. However, if desired, different times can be used. For example, for the object shown when a picture is being made of a chest cavity, a few minutes would be required to obtain sufficient data to produce statistically reliable results, such time being considerably less than that required to obtain images from a large body through a conventional pinhole or collimator structure conventionally used with Anger type cameras or energy intensifiers.

DESCRIPTION OF ALTERNATE EMBODIMENTS

Figure 3:
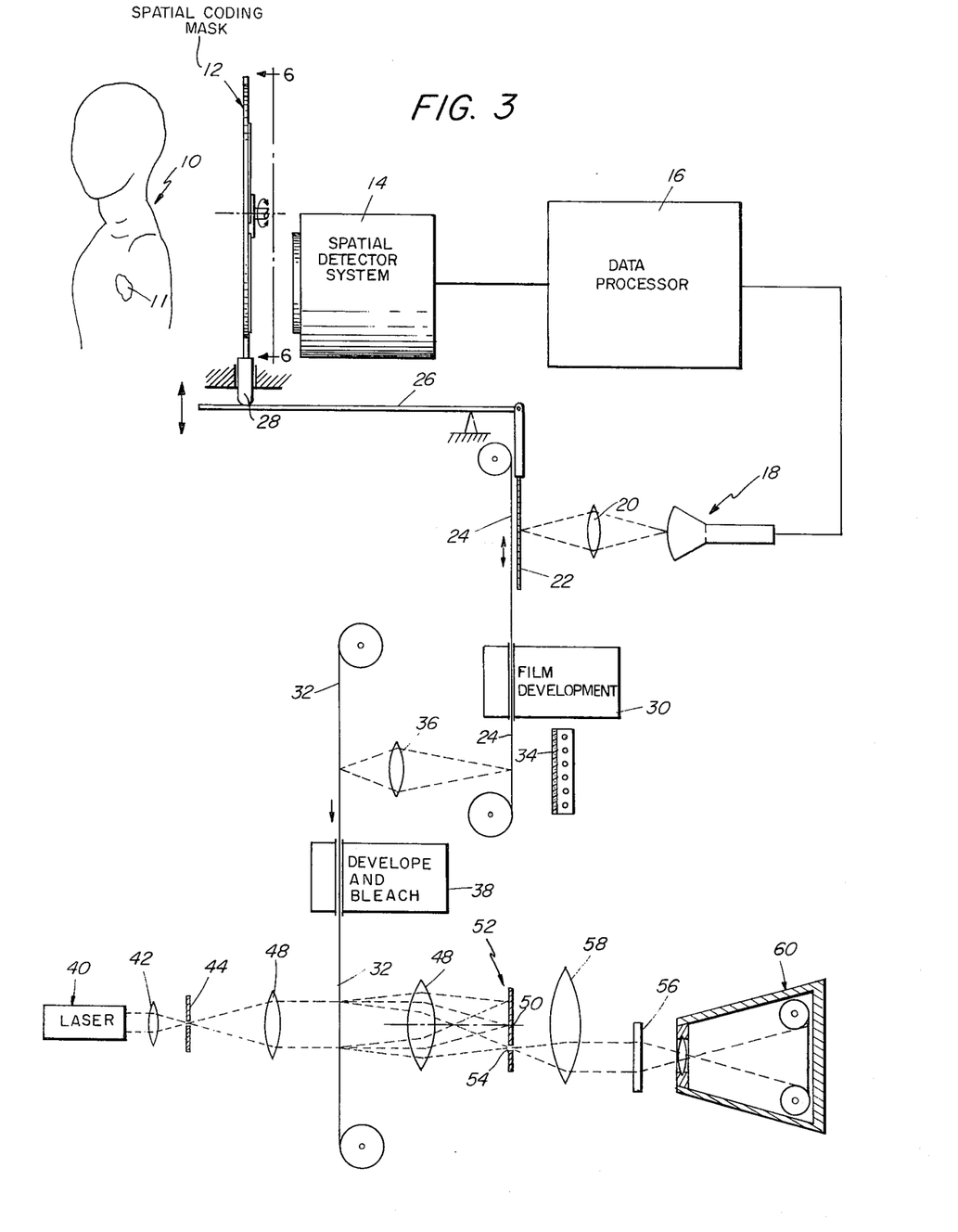
FIG. 3 illustrates a further embodiment of the invention using three different phases of nuclear masks.
Figure 6:
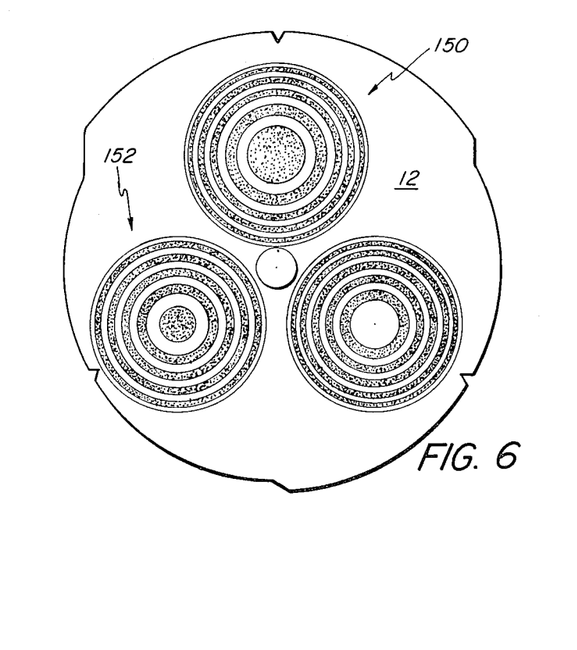
FIG. 6 illustrates a three-phase coding structure for use in the structure of FIG. 3.

Referring now to FIG. 3, there is shown a system like FIG. 1 but with zone plate structure 12 having three zone plates shown in FIG. 6 as a positive zone plate, a 120° shifted zone plate 152 and a 240° shifted zone plate 154. The bar pattern of screen 22 has bars 67 twice the width of the spaces and is shifted vertically one-third of the center to center distance between adjacent bars 67 with each zone plate change and, hence, three sets of bars are recorded on the film 24. The advantage of a three-phase zone plate over a two-phase zone plate is that the positive first order data may be more effectively separated from the negative first order data in the optical reconstruction system with reduction of even order data.

Figure 4:
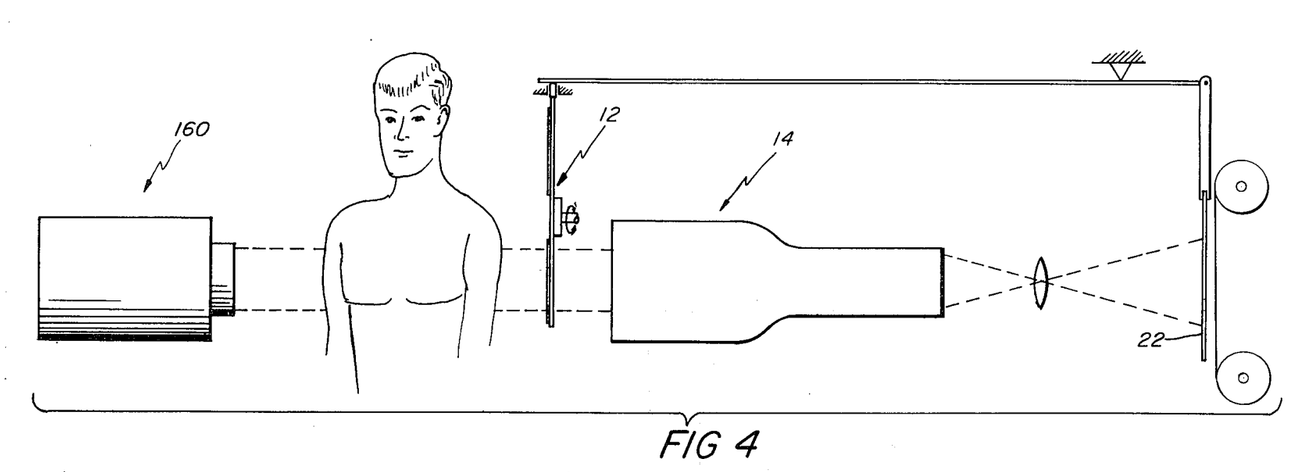
FIG. 4 illustrates a further embodiment of the invention for use with X-rays.

Referring now to FIG. 4, there is shown a further embodiment of the invention where an X-ray source 160 which may, if desired, be of the fluorescent type predominantly concentrated around a predetermined energy level, illuminates an object 10 and a coding structure 12 spatially codes the X-ray passing through object 10. Detector 14 which may be an image intensifier type having a scintillation crystal adjacent a photocathode is illuminated by the coded X-ray pattern and has its output spatially modulated by a bar pattern shifted in synchronization shifting of the zone plates like the system of FIG. 1. Reconstruction is then accomplished substantially in accordance with that disclosed in FIG. 1.

This completes the description of the embodiments illustrated herein. However, many modifications thereof will be apparent to persons skilled in the art without departing from the spirit and scope of this invention. For example, other shapes of masks may be utilized, other types of data amplifiers may be used, and other systems for processing the data may be used. In addition, the optical reconstruction system may, if desired, use noncoherent light, and any desired image construction or pattern recognition technique can be employed. Accordingly, it is intended that this invention be not limited to the particular embodiments illustrated herein except as defined by the appended claims.

What is claimed is:

1. A method of obtaining imaging data of a subject emitting radiant energy comprising the steps of:
   detecting said radiant energy by means of a detector of radiant energy;
   modulating said radiant energy by means of a modulator having a pattern comprising regions relatively opaque to said radiant energy arranged in a pattern with regions relatively transparent to said radiant energy, said modulator facing a predetermined region of said subject and being positioned between said subject and said detector, each of said regions of said modulator being sufficiently thin relative to the distance between said subject and said detector to permit radiant energy emanating from spaced apart points of said subject to cast overlapping shadows of one of said opaque regions upon said detector;
   positioning said opaque regions in a plurality of locations within said modulator while facing said predetermined region of said subject, said detector providing arrays of values of detected radiant energy wherein one of said arrays of values differs from a second of said arrays of values in accordance with the locations of said opaque regions; and
   combining one of said arrays of values with a second of said arrays of values to obtain said imaging data.

2. A system for obtaining imaging data of a subject emitting radiant energy comprising:
   means for detecting said radiant energy;
   means positioned between said subject and said detecting means for spatially modulating said radiant energy, said spatial modulating means having a modulating pattern comprising regions relatively opaque to said radiant energy arranged in a pattern with regions relatively transparent to said radiant energy, each of said regions being sufficiently thin relative to the distance between said subject and said detecting means to permit radiant energy emanating from spaced apart points of said subject to cast overlapping shadows of one of said opaque regions upon said detecting means;

means coupled to said modulating means for positioning opaque regions of said modulating means sequentially in a plurality of locations, said detecting means providing arrays of values of detected radiant energy, one of said arrays of values differing from a second of said arrays of values in accordance with the locations of said opaque regions;

means coupled to said modulating means for signaling the locations of said opaque regions; and means coupled between said signaling means and said detecting means for combining a plurality of said differing arrays of values to obtain said imaging data.

3. A system according to claim 2 wherein said opaque regions are arcuate having individual radii of curvature, the radius of curvature of a repositioned region having a different length from a previous radius of curvature of said region.

4. A system according to claim 2 wherein said opaque regions are arranged around a central point of said pattern, said positioning means imparting a rotation to an individual one of said opaque regions to bring said region from a first of said locations to a second of said locations.

5. A system according to claim 4 wherein said combining means includes means for altering successive ones of said arrays of values in accordance with the locations of said opaque regions, and means for summing together respective points of said altered arrays.

6. A system according to claim 5 wherein said combining means further comprises means for effecting a Fourier transformation of the summation of points of said arrays provided by said summing means.

7. In combination:
means for producing a substantially nonphase coherent spatially coded radiation pattern and for altering a characteristic of said code;
said coded radiation pattern having an energy level above the energy level of radiation in the visible spectrum and said pattern comprising a Fresnel zone pattern; and
means for spatially detecting said radiation pattern and for varying the output of said detecting means as a function of said alteration of said code.

8. The combination in accordance with claim 7 wherein said detecting means comprises an amplifier.

9. The combination in accordance with claim 8 wherein said detecting means comprises a distributed medium for converting said radiation pattern to radiation of a lower energy level than said nonphase coherent spatially coded radiation.

10. In combination:
means for producing a shadowgraph from an object spatially cided with a pattern containing a first phase of a reference signal and a second phase of said reference signal wherein said pattern comprises a Fresnel zone pattern; and
means for deriving an image of an object from said shadowgraph.

11. The combination in accordance with claim 10 wherein said Fresnel zone pattern is a substantially on-center pattern.

12. The combination in accordance with claim 11 wherein said shadowgraph producing means comprises means for producing a bar pattern on a record medium.

13. The combination in accordance with claim 12 wherein said shadowgraph producing means comprises means for converting said spatially coded radiation to radiation of a lower energy level.

14. The method of producing an image of a spatially extensive nuclear radiation source comprising:
forming a shadowgraph of radiation emanating from said nuclear radiation source containing a first phase of spatial reference signal wherein said spatial reference signal comprises a Fresnel zone pattern; and
deriving an image of said source from said shadowgraph.

15. The method in accordance with claim 14 wherein said Fresnel zone pattern is a substantially on-center pattern.

* * * * *